(12) United States Patent
Li et al.

(10) Patent No.: US 6,342,654 B1
(45) Date of Patent: Jan. 29, 2002

(54) USE OF HRMA PROTEINS AND THEIR GENES FOR BROAD RANGE PROTECTION OF PLANTS AGAINST BACTERIAL, FUNGAL AND VIRAL PATHOGENS

(75) Inventors: Qingshun Li; Songhai Shen; Arthur G. Hunt, all of Lexington, KY (US); Sheng Yang He, Okemos, MI (US)

(73) Assignee: University of Kentucky Research University, Lexington, KY (US)

( * ) Notice: Subject to any disclaimer, the term of this patent is extended or adjusted under 35 U.S.C. 154(b) by 0 days.

(21) Appl. No.: 09/444,412

(22) Filed: Nov. 22, 1999

(51) Int. Cl.$^7$ .......................... C12N 5/09; C12N 15/31; C12N 15/82; A01H 5/00
(52) U.S. Cl. ................... 800/279; 800/278; 800/298; 800/288; 435/69.1; 435/468; 435/419; 435/418; 435/320.1; 536/23.1; 536/24.1; 536/23.7
(58) Field of Search .................. 800/279, 278, 800/295, 288; 536/23.1, 23.7, 24.1; 435/69.1, 320.1, 468, 418, 419

(56) References Cited

U.S. PATENT DOCUMENTS

| | | |
|---|---|---|
| 5,576,298 A | 11/1996 | Strobel et al. |
| 5,708,139 A | 1/1998 | Collmer et al. ............. 530/350 |
| 5,750,386 A | 5/1998 | Conkling et al. |
| 5,792,904 A | 8/1998 | Ryals et al. |
| 5,837,685 A | 11/1998 | Strobel et al. |
| 5,858,786 A | 1/1999 | Collmer et al. ............. 435/419 |
| 5,981,843 A | * 11/1999 | Chappell et al. ............. 800/301 |

OTHER PUBLICATIONS

Bennetzen et al, "Approaches and Progress in the Molecular Cloning of Plant Disease Resistance Genes" 1992, Genetic Engineering vol. 14, pp 99–124.*

Linthorst et al, "Constitutive Expression of Pathogenesis –Related Proteins PR–1, GRP and PR–S in Tobacco Has No Effect on Virus Infection", Mar. 1989, The Plant Cell, vol. 1 pp 285–291.*

"Characterization of cis–Acting Sequences Regulating Root–Specific Gene Expression in Tobacco", Yamamoto et al., *The Plant Cell,* vol. 3, 371–382, Apr. 1991.

Proceedings of the National Academy of Sciences of the United States of America, Ham et al., Aug. 18, 1998, vol. 95, No. 17, pp. 10206–10211.

"Propagation of Foreign DNA in Plants Using Cauliflower Mosaic Virus as Vector", Gronenborn et al., *Nature,* vol. 294 (1981); pp. 773–776.

"Evidence That the *Pseudomonas syringae* pv. syringae hrp–Linked hrmA gene Encodes an Avr–Like Protein That Acts in an hrp–Dependent Manner Within Tobacco Cells", Alfano et al., *Molecular Plant–Microbe Interactions,* vol. 10, No. 5, Jul. 1997, pp. 580–588.

"Analysis of the role of the *Pseudomonas syringae* pv. syringae HrpZ harpin in elicitation of the hypersensitive response in tobacco using functionally non–polar hrpz deletion mutations, truncated HrpZ fragments, and hrmA mutations", Alfano et al., *Molecular Microbiology* (1996) 19(4), 715–728.

"Genetic and Transcriptional Organization of the hrp Cluster of *Pseudomonas syringae* pv. phaseolicola", Rahme et al., *Journal of Bacteriology,* vol. 173, No. 2, Jan. 1991, p. 575–586.

"Characterization of the hrp Cluster from *Pseudomonas syringae* pv. syringae 61 and TnphoA Tagging of genes Encoding Exported or Membrane–Spanning Hrp Proteins", Huang et al., *Molecular Plant–Microbe Interactions,* vol. 4, No. 5, pp. 469–476, 1991.

"Nucleotide Sequence and Properties of the hrmA Locus Associated with the *Pseudomonas syringae* pv. syringae 61 hrp Gene Cluster", Heu et al., *Molecular Plant–Microbe Interactions,* vol. 6, No. 5, 1993, pp. 553–564.

\* cited by examiner

Primary Examiner—Phuong T. Bui
Assistant Examiner—Medina A. Ibrahim
(74) *Attorney, Agent, or Firm*—McDermott, Will & Emery (57) ABSTRACT

The use of an avr gene hrmA to induce systematic acquired resistance in plant cells, plant seeds, plant tissues and plants is disclosed. Also disclosed is the use of low level expression of promoters in combination with the hrmA gene to provide broad-spectrum pathogen resistance in plant cells, plant seeds, plant tissues and plants.

7 Claims, 8 Drawing Sheets

Control     TSA-30     TSA-2

FIG. 8(A)     FIG. 8(B)     FIG. 8(C)

USE OF HRMA PROTEINS AND THEIR GENES FOR BROAD RANGE PROTECTION OF PLANTS AGAINST BACTERIAL, FUNGAL AND VIRAL PATHOGENS

This work was supported in part by a grant from the Tobacco and Health Research Institute, University of Kentucky.

TECHNICAL FIELD

The present invention generally relates to the use of HrmA proteins to elicit a hypersensitive response in plant cells, plant seeds, plant tissues and plants. The present invention also relates to the use of pathogen inducible or any promoters with the hrmA gene to express the HrmA proteins in plant cells, plant seeds, plant tissues and plants.

BACKGROUND ART

Plants are capable of combating disease at several levels. In many instances, defense responses are initiated by a specific gene-for-gene interaction, whereby the product of a particular plant defense gene interacts with a corresponding pathogen gene product (elicitor), thereby triggering a series of cellular events that culminate in a localized cell-death response (or hypersensitive response; Dangl et al., 1996; Gilchrist, 1998) and enhanced resistance in unchallenged parts of the plant (SAR; Ryals et al., 1996). The plant gene products involved in gene-for-gene defense mechanisms are typically receptor-like molecules, and the initial interactions of these putative receptors with their ligands (of pathogen origin) is thought to trigger a sophisticated series of signaling events (Bent, 1996; Baker et al., 1997). Among the consequences are increased local production of active oxygen species, accelerated local cell death, induction of salicylic acid and jasmonic acid synthesis, and production, in unchallenged parts of the plant, of a battery of proteins and metabolites that have been associated with enhanced systemic resistance to a broad range of pathogens (Dangl et al., 1996).

The properties of plants that are induced for SAR are attractive from the perspective of pathogen resistance: they are usually protected against a broad range of bacterial, fungal, and viral pathogens, yet they may display little or no harmful effects otherwise (e.g., serious yield losses, aberrant developmental patterns, etc.). As mentioned in the preceding paragraph, challenge with so-called incompatible pathogens, which necessarily leads to a hypersensitive response, induces SAR (Sticher et al., 1997). Challenge with non-pathogenic microbes can also induce SAR (Van Loon et al., 1998). Certain chemicals may be able to induce SAR in treated plants (Gorlach et al., 1996; Morris et al., 1998; Rao and Davis, 1999). The expression of any of a number of genes that, while not of pathogenic origin per se, can induce hypersensitive responses or cause disease-like lesions, can trigger SAR, apparently through a means similar to that by which incompatible pathogens induce SAR (Dangl et al., 1996).

In light of the range of stimuli known to induce SAR, several strategies have been tested to genetically engineer plants so that they are constitutive for SAR, or can be induced with agents not usually associated with disease and defense responses. Expression of both plant resistance and microbial avr genes in the same plant has been tested; when the avr gene is controlled by a promoter whose activity is induced upon challenge by pathogens (including those unrelated to the source of the avr gene), the resulting plants can respond to so-called compatible pathogens as if possessing a specific gene-for-gene system (Hammond-Kosack et al., 1994; 1998). Constitutive expression of genes whose products act downstream from the putative receptors can result in constitutive SAR (Oldroyd and Staskawicz, 1998). Interestingly, in some instances, the resulting plants displayed few (if any) detrimental side effects, indicating that it is possible to condition permanent SAR without seriously affecting plant growth and development, or crop yield (Bowling et al., 1997; Yu et al., 1998; Oldroyd and Staskawicz, 1998). Induced or constitutive expression of microbial avr gene, elicitor or elicitor-like genes and other so-called disease lesion-mimic genes can also induce SAR constitutively in plants (Dangl et al., 1996).

The hypersensitive response of higher plants is characterized by the rapid, localized death of plant cells at the site of pathogen invasion. It occurs during incompatible interactions, which typically involve a microorganism that causes disease only in another plant, and is associated with resistance against many nematodes, fungi, viruses, and bacteria. When HR is induced by a genetically engineered avr gene expressed under the control of a low-level expression promoter or other controlled expression promoters, the responses of the plant are subtle and, most likely, at a microscopic scale.

The avr genes from the species *Pseudomonas syringae* are suitable for the purpose of obtaining genetically engineered SAR. Different strains cause symptoms ranging from galls to "wildfire" blights, and well-characterized virulence (symptom enhancing) factors are as diverse as phytohormones and peptide toxins. Multiple patterns of host specificity (including, in some cases, avirulence (avr)-mediated gene-for-gene interactions) involve virtually all crop plants, and plant associations vary from epephytism to devastating pathogenesis. The interactions with diversified plant specises imply the possibility that avr genes may cause HR in many different plants.

It is now known that that elicitation of the HR by *P. syringae* requires a bacterium that is able to synthesize an Avr protein and to directly inject the Avr protein into the doomed plant cell. (See He, 1998, Ann. Rev. Phytopathol., 36:363–392). The ability of *Pseudomonas syringae* strains to elicit the HR or pathogenesis in nonhost or host plants, respectively, is controlled by the hrp genes, and typical Hrp mutants have the null phenotype of a nonpathogen in all plants. [See *Proc. Nat'l. Acad. Sci. USA,* 82:406 (1985); *J. Bateriol.,* 168:512 (1986); and *Mol. Plant—Microbe Interact.,* 4:132 (1991)]. Hrp genes are clustered, and some appear to be widely conserved in Gram-negative bacterial pathogens that cause eventual necrosis in their hosts. These pathogens include *Pseudomonas syringae, Pseudomonas solancearum, Xanthomonas campestris, Erwinia amylovora, Erwinia stewartii,* and *Erwinia chrysanthemi.* [See *Mol. Plant—Microbe Interact.,* 5:390 (1992)]. The hrp clusters from *Pseudomonas syringae* pv. *syringae* 61 (which has been deposited with the American Type Culture Collection under the provisions of the Budapest Treaty and which is designated as ATCC 55427) encode for proteins that assemble the type III secretion system to deliver Avr protein into plant cells. Through genetic engineering, the avr gene can be expressed inside the plant cell, thus by passing the delivery system that is required in native bacterial system. As a result, the avr genes from *P. syringae* can thus be used to obtain even broad range protection in plants.

The present inventors have discovered that it is desirable to express a broad-spectrum avr gene that can elicit resistance response in many cultivars and plant species so that the same avr expression construct can be used to generate resistance in multiple plants and cultivars. Many avr genes are identified initially based on their ability to trigger the HR and resistance in one or a few cultivars of a given plant species (Leach and White, 1996). However, further examination of the avirulence effect of these avr genes on other plant species often uncovers additional plant species and cultivars that react with an HR to these avr genes. To date, more than 50 pathogen avr genes (most from bacteria) have been cloned and characterized. These avr genes provide a useful resource for genetic engineering of broad-spectrum resistance in many crop plants. The hrmA gene is a broad-spectrum avr gene; it has been shown to trigger an HR in all examined tobacco cultivars (Alfano et al., 1997) and transformed *Arabidopsis thaliana* (Q. Li and S. Shen, unpublished observation). The present inventors have also discovered that a pathogen-inducible plant promoter with a very low basal level of expression (estimated in between $10^{-7}$–$10^{-4}$ of poly(A) RNA) can allow this strategy to work. The present inventors have demonstrated the use of the Δ0.3TobRB7 promoter sequence to express the highly potent HR elicitor gene, hrmA. However, a large collection of pathogen-infection-specific promoters can be used to make the inducible expression, or low-level non-inducible expression promoters can be used to make constitutive expression, of avr genes more versatile in different plants, tissues, and/or developmental stages. The expression of the avr genes, in particular example of this patent hrmA, would induce SAR thus warrant a new methods to genetically engineer SAR in crops.

SUMMARY OF THE INVENTION

The invention provides a method of increasing resistance of plants to pathogens that involves introducing avr genes into plants and expressing avr proteins.

The invention thus provides novel chimeric gene constructs that contain avr coding sequences.

The invention also provides transformed plant cells, plant seeds, plant tissues and transgenic plants transformed with novel chimeric gene constructs that contain the avr coding sequences.

The invention thus provides a method for the expression of the avr genes in plant cells, plant seeds, plant tissues and plants.

The invention also provides the use of pathogen inducible promoters, or any promoter to express the avr genes in plant cells, plant seeds, plant tissues and plants.

According to an embodiment of the invention, a bacterial HR elicitor, hrmA of *P. syringae* and homologeus thereof, are expressed in plants such as tobacco under the control of a promoter, such as Δ0.3TobRB7, which is expressed in low-level constitutively. A forced expression of the HR in otherwise susceptible plants leads to increased resistance to pathogen infection.

Additional advantages of the present invention will be set forth in the description and examples that follow, or may be learned from practicing the invention. These and other advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further advantages, will best be understood by reference to the following detailed description taken in conjunction with the accompanying drawings.

BRIEF DESCRIPTION OF THE DRAWINGS

FIG. 2. Appearance of transgenic plants carrying the TSA construct. (A) Comparison of T1 plants derived from the TSA-2 and TSA-30 primary transformants with a transformed control. (B) Close-up of an older leaf from a TSA-2 plant showing the necrosis that occasionally appears. The arrows point to some examples of the necrosis spots.

FIG. 5. Levels of free (A) and total (B) salicylic acid in control and hrmA transgenic plants. Transformed control and kanamycin resistant T1 progeny of the TSA-2 and TSA-30 plants were sampled and SA determined as described in Methods. SA for each line was determined in triplicate.

FIG. 6. Resistance of hrmA transgenic plants to viral pathogens. (A) Appearance of inoculated leaves of controls and representative TSA-2 plants, showing the HR-like necrosis that is characteristic of the TSA plants. The photograph was taken one day after inoculation with the indicated virus. (B) Comparison of an upper (systemic) leaf from a TVMV-inoculated control and a TSA-30 plant, showing the characteristic TVMV symptoms on the control, and lack thereof on the TSA-30 plant. (C) Immunoblot determination of TVMV and TEV coat protein levels in plants inoculated with TVMV and TEV. Samples were taken two weeks after inoculation.

FIG. 7. Resistance of hrmA transgenic plants to wild fire disease caused by *P. syringe* pv. *tabaci* WF4. (A) Growth of *P. syringae* pv. *tabaci* on inoculated TSA-2 or control plants. The data represent the mean of three replicate experiments; standard deviations for each point are shown as well. (B) Lesions caused by infiltration with different dilutions of *P. syringae* pv. *tabaci* bacteria suspensions. An original suspension with an OD (600 nm) of 1.0 was diluted 1,000 times (spot 1), 5,000 times (spot 2), and 10,000 times (spot 3). Spot 4 is a buffer control.

DETAILED DESCRIPTION OF THE INVENTION

SEQ ID NO. 1 is the nucleotide sequence of *Pseudomonas syringae* pv. *syringae* 61 hrmA gene (from Heu et al., which discloses the nucleotide sequence for the hrmA locus associated with the *Pseudomonas syringae* pv. *syringae* 61 hrp cluster and the characterization of the physical and phenotypic properties of the gene product). The deduced amino acid sequence is shown by SEQ ID NO. 2.

Recognition of pathogen avirulence (Avr) factors by plant resistance gene products triggers disease resistance response in plants. The hrmA gene from *Pseudomonas syringae* pv. *syringae* has previously been shown to confer avirulence on the virulent bacterium *P. syringae* pv. *tabaci* in all examined tobacco cultivars. Basal level expression of the hrmA gene in tobacco plants under the control of the tobacco Δ0.3TobRB7 promoter activates the expression of pathogenesis-related genes, accumulation of salicylic acid, and the transgenic plants exhibit high levels of resistance to multiple leaf pathogens: tobacco vein mottling virus, tobacco etch virus, black shank fungus *Phytophthora parasitica*, and wild fire bacterium *Pseudomonas syringae* pv. *tabaci*. Thus, controlled low level expression of bacterial avr genes, such as hrmA, can be used in plants to generate broad-spectrum resistance to bacterial, fungal and viral pathogens.

During host-pathogen co-evolution, many plants have acquired disease resistance genes whose products are involved directly or indirectly in the recognition of pathogen-derived molecules called avirulence factors (Staskawicz et al, 1995). Recognition of pathogen avirulence factors by the plant resistance gene products results in activation of plant disease resistance responses, including often a localized plant cell death response known as the hypersensitive response (HR) (Goodman and Novacky, 1994; Dangl et al., 1996; Lamb and Dixon, 1997). In plant pathogenic bacteria, the function of avr genes is dependent on hypersensitive response and pathogenicity (hrp) genes (Leach and White, 1996). Many hrp genes are involved in regulation and assembly of a type III protein secretion system (He, 1998). Growing indirect evidence suggests that bacterial Avr proteins are delivered directly into the plant cell via the Hrp system (He, 1998; Collmer, 1998; Bonas and Van den Ackerveken, 1999). For example, the hrmA gene of *Pseudomonas syringae* pv. *syringae* confers broad-spectrum avirulence on *P. syringae* pv. *tabaci* in all examined susceptible host tobacco (Alfano et al., 1997). The avirulence function of the hrmA gene is dependent on hrp genes (Heu and Hutcheson, 1993; Alfano et al., 1997). Purified HrmA protein does not trigger the HR when infiltrated into the apoplast of tobacco leaves; however, transient expression of the hrmA gene directly in tobacco cells results in cell death, suggesting recognition of HrmA inside the tobacco cell (Alfano et al., 1997).

Constitutive high-level expression of an avr gene in resistant plants results in a systemic HR and the transgenic plants die, as was observed for transgenic expression of the *P. syringae* pv. *glycinea* avrB gene in the resistant *Arabidopsis thaliana* ecotype Columbia (Gopalan et al., 1996). The present inventors have discovered, however, that controlled expression of avr genes at very low levels or in response to virulent pathogen infection may be used to generate plant disease resistance without causing significant and constitutive damage to uninfected plant tissues. The tobacco Δ0.3TobRB7 promoter sequence was previously shown to be induced specifically at the feeding site of root-knot nematodes (Opperman et al., 1994). The basal level expression of this promoter sequence was apparently very low and was undetectable based on β-glucuronidase activity assay in transgenic tobacco plants. The very low level of basal expression (estimated level between $10^{-7}$–$10^{-4}$ of poly(A) RNA) and induction by nematode infection make the Δ0.3TobRB7 promoter sequence an excellent candidate for testing the feasibility of low level and conditional expression of avr genes for generating disease resistant plants. The basal level of hrmA expression may trigger expression of systemic acquired resistance against pathogens thus preventing further disease development.

Experimental Results

Production and Characterization of hrmA-Transgenic Tobacco Plants

Figure 1:
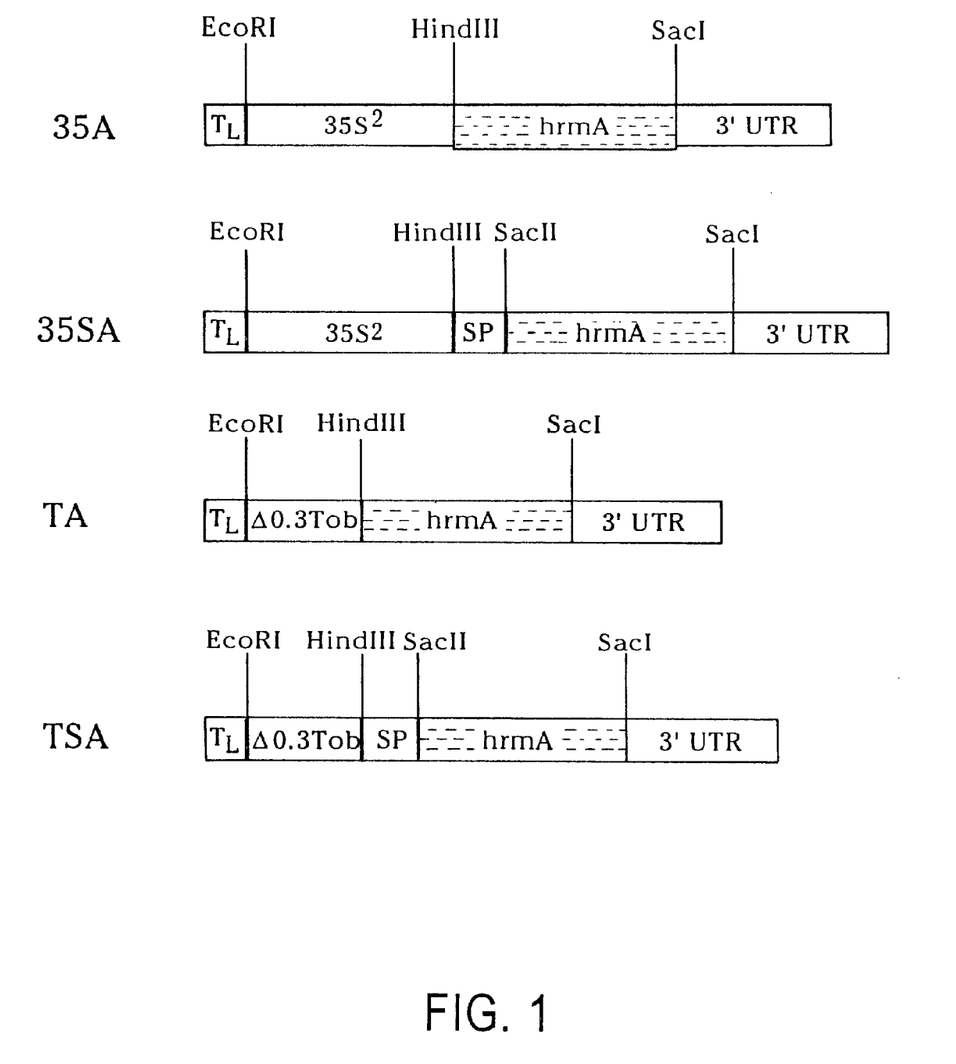
FIG. 1. A schematic representation of hrmA-T-DNA constructs in the binary vector pKYLX7.1. The positions of the T-DNA left border (TL), double 35S promoter ($35S^2$), Δ0.3TobRB7 promoter (Δ0.3Tob), the Pr-1b signal peptide genes (SP), hrmA gene, and the 3' UTR (from pea rbcS gene) are illustrated. Not shown next to the right side of the construct is the NPTII gene (for Kanamycin resistance) expression cassette and the T-DNA right border.

The *Pseudomonas syringae* hrmA gene is modified for expression in plants as shown in FIG. 1. Several different variations are tried, as indicated. Two constructs consist of the hrmA gene under the control of the modified 35S promoter present in pKYLX71:35S$^2$ (Maiti et al., 1993). One of these includes the pathogenesis related protein signal peptide (Cornelissen et al., 1986) suited for targeting of the predicted gene product to the endomembrane system (and presumably to the apoplast). These constructs are termed 35A and 35SA, respectively (FIG. 1). In two other constructs, the modified 35S promoter was replaced with the Δ0.3TobRB7 promoter (Opperman et al., 1994). This promoter has been reported not to express without the challenge of roots with root-knot nematodes. One of the Δ0.3TobRB7 constructs (TA) consists of just the promoter flanked by the hrmA gene, which is expected to express the HrmA protein intracellularly. A second construct (TSA) contains a PR-1b signal peptide (SP) at the N-terminus of the hrmA coding region.

An attempt to introduce the 35A and 35SA chimeric genes into plants using *Agrobacterium tumefaciens* was unsuccessful. When leaf explants are treated with Agrobacteria carrying the 35A or the 35SA construct, no transgenic callus was obtained. This is consistent with the previous finding by Alfano et al. (1997) that high level expression of the HrmA protein leads to hypersensitive cell death in tobacco cells. Of special interest is the observation that inclusion of the signal peptide does not permit the isolation of transformants.

Figure 2A:
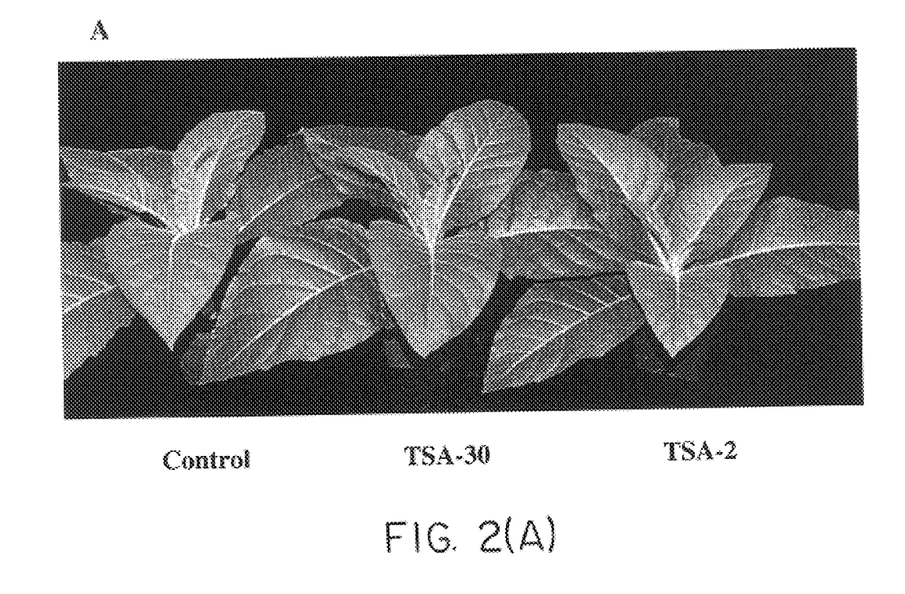
Figure 2B:
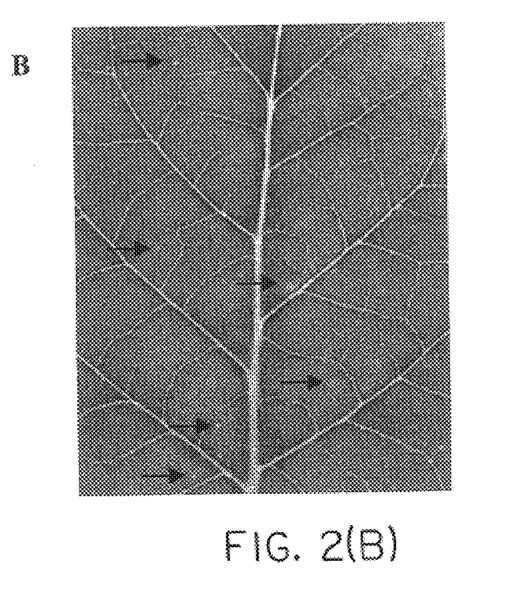

No transgenic plants were obtained with Agrobacteria carrying the TA construct, suggesting that the basal level of intracellular hrmA expression under the control of Δ0.3TobRB7 was still detrimental to plant growth or development. This result is somewhat surprising, because the Δ0.3TobRB7 promoter was reported to be active only in giant nurse cells formed in roots as a consequence of invasion by nematodes (Opperman et al., 1994). However, Agrobacteria that carry the TSA construct yield a small number of viable transformant lines, possibally due to the signal peptide that leads the HrmA protein to be secreted outside the cell membrane where HrmA may not function as an Avr factor (as found by Alfano et al., 1997). Thus, the signal peptide reduces hrmA concentration inside the cell by mediating the translocation of newly synthesized protein outside the cell membrane. Southern blot analysis confirms that these plants carry the transgene (data not shown). The six independent TSA lines can be classified into 3 types: 1) plants displaying normal growth, 2) plants displaying severe stunting and necrosis (not shown), and 3) plants displaying minor alterations in growth (lines 2 and 30, FIG. 2A). Line 2 shows a near-normal growth with slightly rigid leaves and with some micro-lesions on older leaves (FIG. 2B). Line 30 shows a modest retardation of root system development. However, once roots are established, TSA-30 is indistinguishable from control plants (FIG. 2A), and lacks the micro-lesions that typify the plants from line 2.

The altered growth habit of transgenic plants is independent of any challenge by nematodes, suggesting that the Δ0.3TobRB7 promoter ret ains a low level of activity in the absence of nematode infection. To confirm this, the expression level of the hrmA gene in all transgenic lines was examined. The present inventors found that hrmA mRNA cannot be detected in any of the transgenic plants by northern analysis, presumably due to low levels of expression (not shown). However, reverse transcription-polymerase chain reaction (RT-PCR) combined with Southern blot analysis is effective in detecting the hrmA mRNA in transgenic leaves and roots; thus hrmA is expressed constitutively in these plants (FIG. 3), but at low levels below the detection of northern blot analysis. The apparent hrmA expression level is much higher in the TSA-2 line than in the TSA-30 line, which is consistent with the appearance of micro lesions in TSA-2, but not in TSA-30.

Expression of Pathogenesis-related Genes

Figure 3:
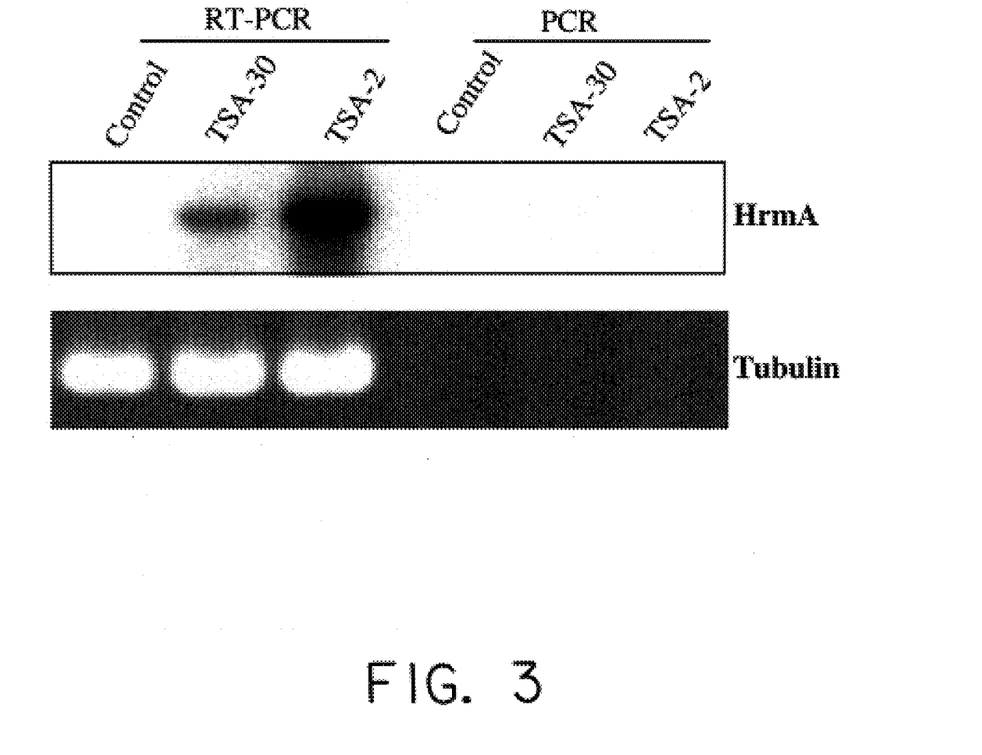
FIG. 3. Expression of the hrmA gene in the TSA-2 and TSA-30 transgenic lines. hrmA or β-tubulin transcripts were amplified by RT-PCR as described in Methods. hrmA band were detected by Southern blotting using hrmA-specific radioactive probe. The DNA products corresponding to amplification products of the β-tubulin gene were visualized by ethidium bromide staining. PCR without prior reverse transcription was used as control to confirm that the RT/PCR products were attributable to RNA. Lanes containing the products of RT/PCR and PCR are denoted above the gels. For comparison, RNA isolated from the transformed control was also analyzed.
Figure 4:
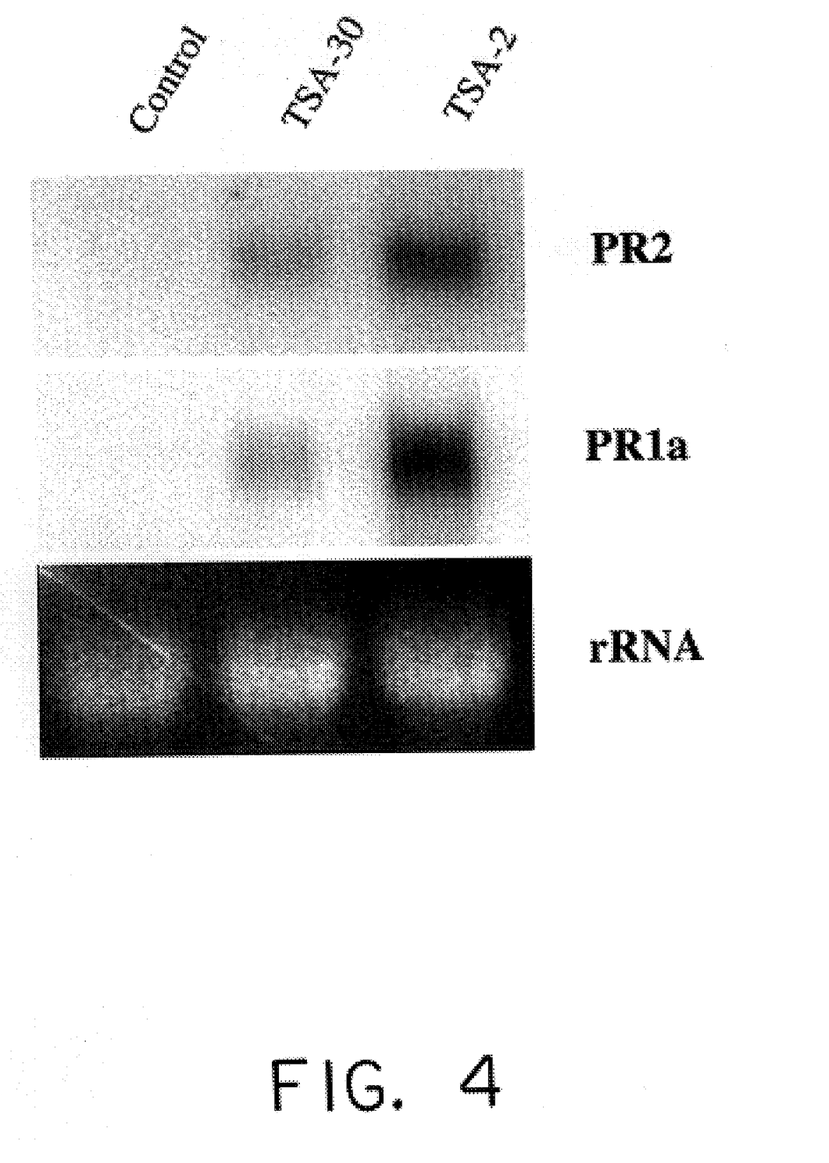
FIG. 4. Expression of pathogenesis-related genes in TSA-2 and TSA-30 plants. Total RNA was isolated from kanamycin-resistant T1 progeny of the TSA-2 and TSA-30 plants or from transformed control plants. 20 μg of total RNA was analyzed by northern blotting, using tobacco pr1 and pr2-specific probes as described in Methods. The ethidium bromide-stained 18S rRNA is shown as a loading control.

The appearance of micro lesions on old leaves of TSA-2 and delayed root development in TSA-30 suggest that low-level constitutive expression of the hrmA gene in these plants leads to induction of hypersensitive and systemic defense responses. To confirm this, the levels of expression of two pathogenesis-inducible genes in vector-transformed control plants and in TSA-2 and TSA-30 plants are measured. When RNA from leaves of TSA-2 and TSA-30 plants is hybridized with probes of PR-1a and PR-2 (encoding β-1,3-glucanase), constitutive expression of these genes is observed in the TSA lines, but not in the control plants (FIG. 4). Moreover, there is a positive correlation between the levels of expression of these two genes in the TSA lines (FIG. 4) and the quantities of hrmA RT-PCR product that are observed (FIG. 3). Thus, it appears that hrmA gene expression, even at very low levels, is sufficient for the induction of defense responses.

Figure 5A:
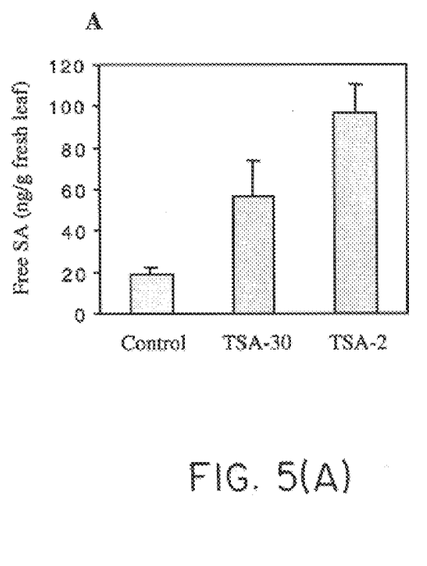
Figure 5B:
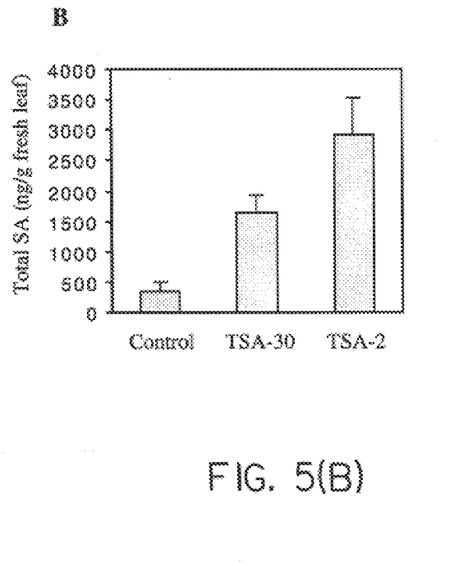

In wild-type plants, the induction of the pathogen related PR-1 and PR-2 genes by incompatible pathogens is mediated by salicylic acid, the synthesis of which is dramatically increased as a consequence of the activation of defense responses. The induced expression of PR-1 and -2, salicylic acid, are the indicators of SAR (see Sticher, et al., Systemic acquired resistance, *Ann. Rev. Phytopathol*, 35, 235–270 (1997). To better understand the means by which hrmA expression induces PR-1 and PR-2 expression, the levels of salicylic acid in the TSA-2 and TSA-30 plants is compared with the levels in control plants. As shown in FIG. 5, the levels of free and total salicylic acid in the TSA plants are greater than those seen in controls. This is especially true for the TSA-2 plants, which also have the highest levels of PR gene (FIG. 4) and hrmA (FIG. 3) expression. These observations demonstrate that low-level hrmA expression induces local and systemic defense responses in the TSA plants.

Resistance to Virulent Pathogens

The constitutive expression of the PR-1 and PR-2 genes in leaves of the TSA-2 and TSA-30 lines (FIG. 4), and the elevated levels of salicylic acid and its conjugates in the TSA plants (FIG. 5), suggest that these lines exhibit enhanced resistance to various pathogens. This is examined by studying the responses of these lines to two viruses (tobacco vein mottling virus [TVMV] and tobacco etch virus [TEV]), a bacterial pathogen, *Pseudomonas syringae* pv. *tabaci,* and a fungal pathogen, *Phytophthora parasitica*.

Figure 6A:
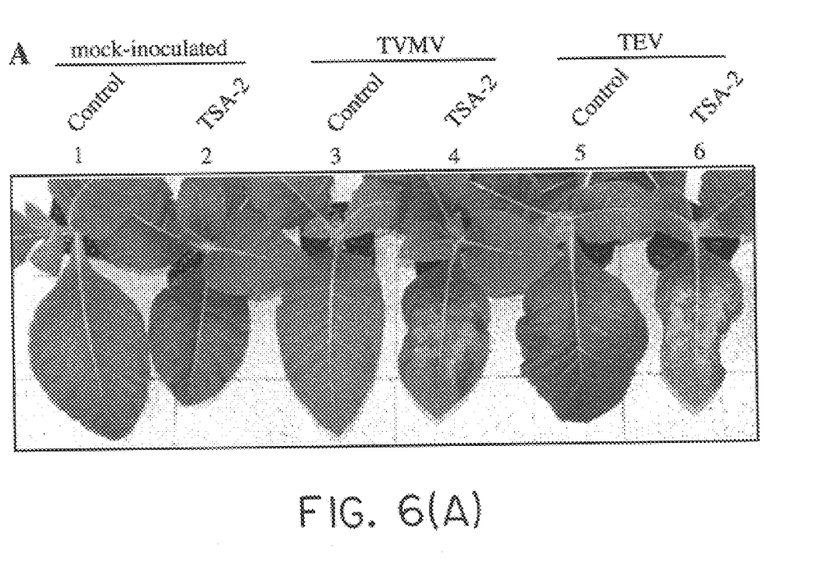

Two differences between the TSA lines and the control line are observed when plants of each line are inoculated with either of the two viruses. Within one day of inoculation, the TSA lines exhibit HR-like necrosis on the leaves that had been inoculated with TVMV or TEV (FIG. 6A). The HR necrosis is restricted to the inoculated leaf tissue (FIG. 6A). This necrotic response is characteristic of just the TSA plants. In numerous previous inoculation studies with TVMV and TEV (Xu et al., 1997 and 1998; Fellers et al., 1998; Maiti et al., 1993), such effects have never been observed with other tobacco lines, transgenic or otherwise.

Figure 6B:
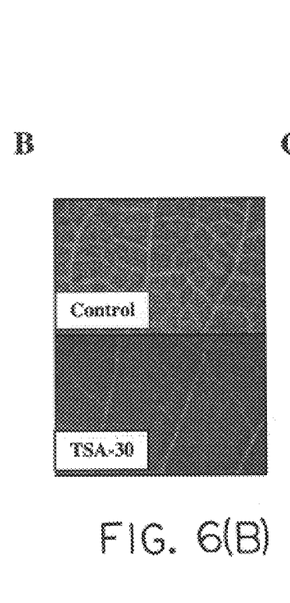
Figure 6C:
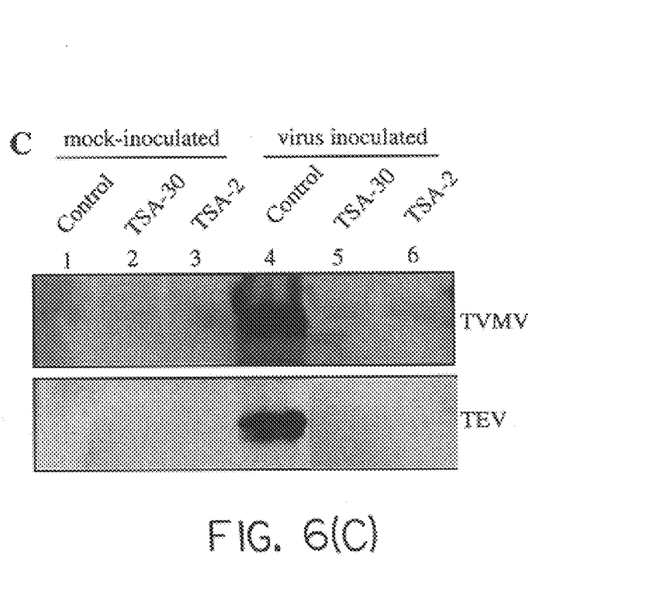

Beginning about five days post-inoculation, typical vein mottling or leaf etch symptoms are invariably detected on the uninoculated upper leaves of control plants that had been infected with TVMV (FIG. 6B) or TEV. In contrast, the uninoculated upper leaves of infected TSA-2 or TSA-30 plants remain free of disease symptoms (FIG. 6B). Moreover, virus accumulation, as judged by the presence of virus coat protein, could not be detected in the TSA-2 or TSA-30 plants (FIG. 6C). In contrast, considerable coat protein is detected in the upper leaves of infected control plants (FIGS. 6C). These results demonstrate that, after the initial hypersensitive reaction to infection that is seen in the inoculated leaf, the TSA plants are wholly resistant to further systemic spread of TVMV and TEV.

Figure 7A:
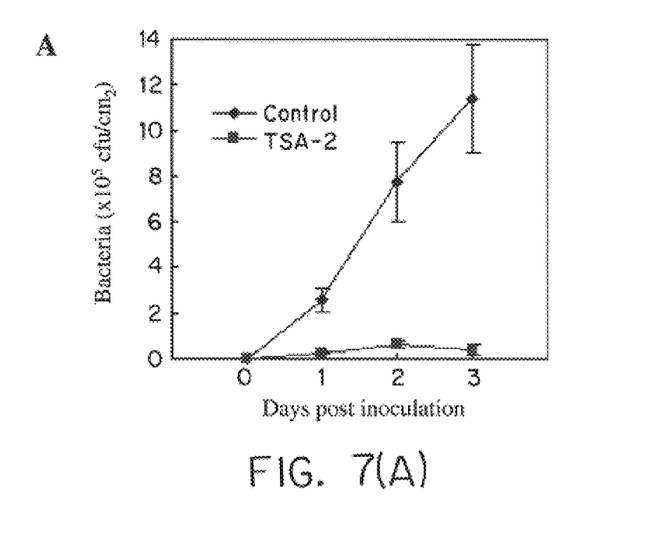
Figure 7B:
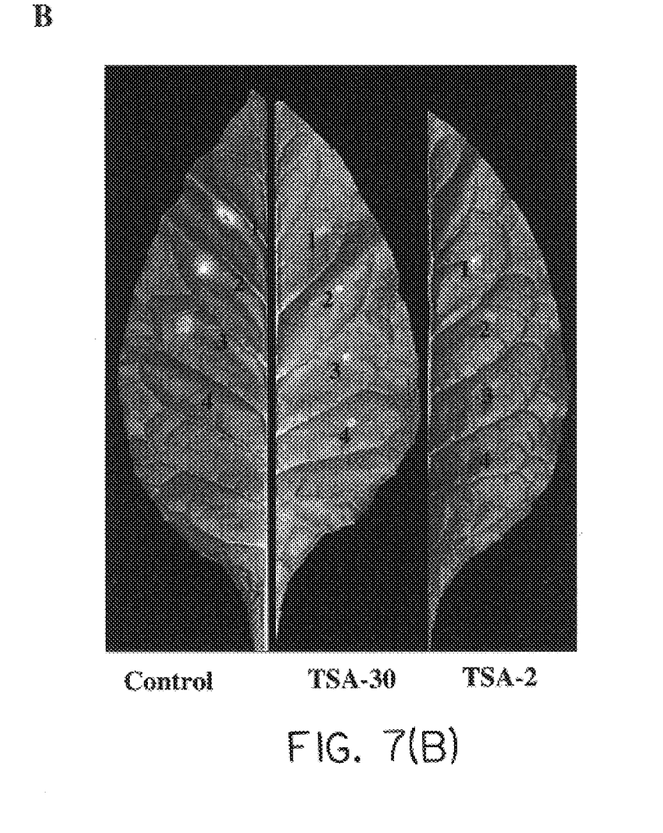

To study the susceptibility of the TSA lines to bacterial diseases, experiments are performed with *Pseudomonas syringe* pv. *tabaci,* the wild fire disease pathogen. After inoculation of control plants, the bacterial population at the inoculation site is found to increase in a linear fashion over the course of three days (FIG. 7A), and characteristic symptoms (spreading necrosis and chlorosis) are apparent at these sites (FIG. 7B, left panel). In contrast, no bacterial growth is seen in inoculated TSA-2 plants, and symptoms indicative of disease are conspicuously absent on inoculated TSA-2 (FIG. 7B, right panel) and TSA-30 (FIG. 7B, middle panel) plants. TSA plants exhibit a HR-like necrosis at the site of inoculation; this necrotic response is also observed when plants are mock-inoculated.

Figure 8A:
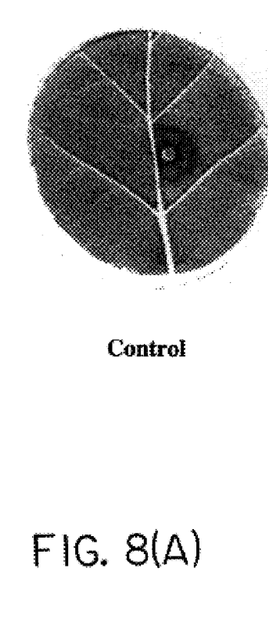
FIGS. 8(A)–8(C). Resistance of hrmA transgenic plants to the fungal pathogen *Phytophthora parasitica* var. *nicotianae* isolate 62. TSA-2 and TSA-30 plants were compared with a transformed control, as described in Methods.
Figure 8B:
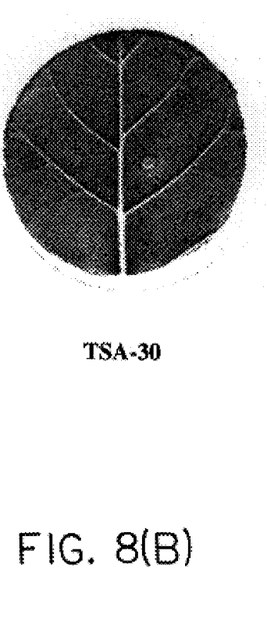
Figure 8C:
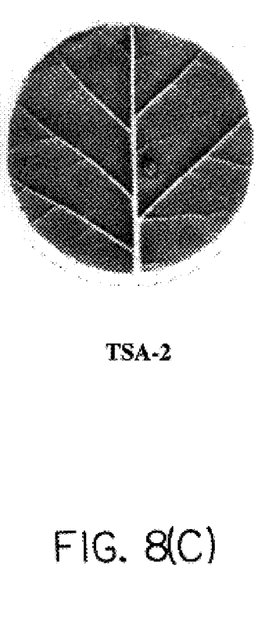

To study the susceptibility of the TSA lines to fungal diseases, TSA and control plants are inoculated with plugs of media containing *Phytophthora parasitica* var. *nicotianae* isolate 62, the black shank disease pathogen. Four days after inoculation of a control plant leaf, a necrotic area with a 20 mm diameter is apparent, indicative of successful infection by this pathogen (FIG. 8). In contrast, cell death is restricted to the leaf tissue that was touched by the pathogen plug in leaves from TSA-30 and TSA-2 plants, indicative of a local hypersensitive response (FIG. 8). Moreover, these leaves are devoid of the fungus (not shown). Thus, the TSA plants display resistance to *P. parasitica,* again consistent with the constitutive expression of PR genes and resistance to the viral and bacterial pathogens tested.

In summary, low level expression of a bacterial HR elicitor may thus be used as a means for controlling disease. Low-level constitutive expression of the hrmA gene yields plants that possess high levels of resistance against a broad range of microbial plant pathogens without significantly affecting normal plant growth and development. Specifically, transgenic lines 2 and 30 exhibit near-normal growth and are highly resistant to TVMV, TEV, P. s. pv. *tabaci,* and *P. parasitica*. The most dramatic response of hrmA transgenic plants to pathogen inoculation is an HR-like necrosis at the site of pathogen inoculation, irrespective of whether or not inoculated pathogens normally induce necrosis in tobacco. For example, TVMV and TEV normally cause systemic vein mottling and leaf etch, but not necrosis in tobacco; the hrmA transgenic plants, in contrast, respond to virus inoculation with a rapid, localized HR-like necrosis, and the viruses are unable to spread beyond the inoculated sites. A similar necrotic response is observed when the hrmA transgenic plants are inoculated with bacterial and fungal pathogens. The mechanism by which this response is triggered remains unclear. One possibility is that pathogen infection increases the expression of hrmA gene at the inoculation site. The increased hrmA expression would then activate a higher level of defense responses, including the appearance of a macroscopic HR. Alternatively, a low level of hrmA gene expression in the transgenic plants may partially activate defense mechanisms, including the HR cell death program. Consistent with this prediction, hrmA plants constitutively express PR genes, elevated salicylic acid level, and in TSA-2 plants, micro HR-like lesions are present in old leaves. These transgenic plants are now hypersensitive to certain environmental stresses, e.g., infection by virulent pathogens, that alone normally are not sufficient to activate the HR cell death program and other defense responses.

In several respects, the hrmA transgenic line TSA-30 shows hallmarks of the *Arabidopsis thaliana* cpr (for constitutive PR gene expression) class of mutants that constitutively express defense genes and exhibit heightened resistance to pathogen infection (Clarke et al., 1998). TSA-2, on the other hand, exhibits some features of the 'lesion mimic' class of mutants of maize, barley, tomato, and *Arabidopsis thaliana* (Neuffer and Calvert, 1975; Hoisington et al., 1982; Walbot et al., 1983; Wolter et al., 1993; Dietrich et al., 1994; Greenberg et al., 1994; Bowling et al, 1994 and 1997). In 'lesion mimic' mutants, HR-like lesions and host defense mechanisms are activated in the absence of a pathogen. The cpr and 'lesion mimic' classes of mutants as well as the hrmA transgenic plants are effective in containing pathogen infection.

Alfano et al. (1997) showed that intracellular expression of the hrmA gene triggers HR cell death in tobacco, whereas infiltration of purified HrmA protein to the apoplast of tobacco leaves does not. It was therefore suggested that HrmA acts inside the plant cell to trigger HR. The present experiments did not generate transgenic tobacco plants that produce the HrmA protein intracellularly. However, a number of transgenic plants that presumably express the HrmA protein extracellularly were generated, but the number was unexpectedly small. The difficulty in producing transgenic plants that express HrmA extracellularly was unexpected, given that HrmA does not appear to elicit HR from outside of the tobacco cell. A likely explanation is that the transport of the pre-HrmA polypeptide is somewhat less than 100% efficient; this, along with a low level of constitutive activity of the Δ0.3TobRB7 promoter, would result in levels of intracellular HrmA high enough to kill many transformed cells.

An additional surprising finding was the low-level activity of the Δ0.3TobRB7 promoter in the hrmA plants. A previous study (Opperman et al., 1994) indicated that this promoter was active only in giant cells, with undetectable levels of expression in other cells. The present experiments show that the Δ0.3TobRB7 promoter is active at levels beneath the sensitivity of the GUS reporter system, but detectable by more sensitive methods (such as RT/PCR). This constitutive expression is apparently the reason why plants designed to express intracellular HrmA could not be produced. However, we need to point out that the Δ0.3TobRB7 is not necessarily required for the succuss of the low expression of hrmA gene. In theory, any promoter conferring that level expression, or other stronger promotes regulated to express in low levels may also lead to the right level expression of hrmA or other similar avr genes.

Experimental Methods

DNA Manipulations

Recombinant DNA manipulations are performed basically as described by Sambrook et al. (1989). Tobacco (*Nicotiana tabacum* cv. Wisconsin 38) genomic DNA is used as template for amplification of the Δ0.3TobRB7 promoter (Yamamoto et al., 1991 and Opperman et al., 1994). Oligonucleotide Δ0.3TobRB7-5' (G GAATTCAGCTTATCTAAACAAAGTTTTAAATTC) (SEQ ID NO.6) and Δ0.3TobRB7-3' (GT AAGCTTCTGAGCGATCCTTCTCACTAGAAAAATGCCC) (SEQ ID NO. 7) are used in polymerase chain reaction (PCR). The PCR product is then digested with EcoRI and HindIII (sites underlined in the primer sequences), and cloned into pBluescript KS+ (Stratagene). DNA sequencing data shows that the insert matches the expected sequence.

The signal peptide sequence of pathogenesis-related protein 1b (PR-1b) is amplified by PCR using *N. tabacum* cv. Samsun NN genomic DNA as template and oligonucleotides PR-1b-5' (CACG AAGCTTACCATGGGATTTTTTCTCTTTTCAC (SEQ ID NO. 8), Hind III site underlined) and PR-1b-3' (TC CCGCGGGAGTTTTGGGCATGAGAAG (SEQ ID NO. 9), SacII site) as primers (Cornelissen et al., 1986). The amplified sequence is cloned into pBluescript SK+. The cloned PR-1b signal peptide sequence is confirmed by DNA sequencing.

The hrmA gene is also amplified by PCR, using *Pseudomonas syringae* pv. *syringae* strain 61 genomic DNA as template and two PCR primers designed according to the hrmA sequence (Heu and Hutcheson, 1993). Two 5' primers are made with different restriction sites for cloning with or without the PR-1b signal peptide sequence (FIG. 1) (hrmA-5'-1, CACGAAGCTTACCATGGACCCTATCCATGC (SEQ ID NO. 3), and hrmA-5'-2,TCCG CCGCGGGGTGAACCCTATCCATGC (SEQ ID NO. 4), HindIII and SacII sites underlined). The 3' primer sequence is hrmA-3', GTGGAGCTCAGTTTCGCGCCCTGAG (SEQ ID NO. 5) (SacI site underlined). The full-length hrmA DNA is first cloned into pBluescript KS+ and the insert is verified by DNA sequencing. Various combinations of promoters, signal peptide sequences, and the hrmA gene are then made in the T-DNA binary vector pKYLX71: 35S$^2$ (Mogen et al., 1992; Maiti et al., 1993). 50 mg/l kanamycin is used as plant transformation selection marker. FIG. 1 shows the various expression cassettes constructed.

Tobacco Transformation and Plant Growth Conditions

The resulting pKYLX71: 35S$^2$ derivatives are mobilized into *Agrobacterium tumefaciens* (pGV3850) and the transconjugants used to transform tobacco (*Nicotiana tabacum* L.) cv. KY14 as described in detail elsewhere (Li and Hunt 1995). Transgenic plants are grown in a standard growth chamber for a few weeks before moving to a greenhouse to produce seeds. All leaf pathogen inoculation experiments are carried out in a growth chamber with 16-hour lightness and 8-hour darkness and 22–25° C. The nematode inoculation tests are done in a green house. KY14 plants transformed with the vector pKYLX71: 35S$^2$ are used as control in all experiments.

Detection of Expression of hrmA and PR Genes

Reverse transcription followed by polymerase chain reaction (RT-PCR) is used for hrmA transcript detection. Total RNA is isolated from the transgenic plants using the TRIzol™ Reagent kit (GIBCO BRL). To remove possible DNA contamination, the total RNA is treated with DNase then heated at 70° C. for 10 min to inactivate the DNase, followed by phenol:chloroform extraction and ethanol precipitation. 5 g purified total RNA is added to a 30 μl reverse transcription mixture and oligo dT is used as the first strand primer. The resultant first strand is used as PCR template and primer PR-1b-5' and hrmA-3' is used to amplify hrmA DNA. The PCR products are separated in a 1% agarose gel and blotted to Nytran Plus membranes (Schleicher & Schuell Inc.), and then probed by [$\alpha$-$^{32}$P]-dCTP labeled hrmA DNA. Tobacco-tubulin DNA is also amplified from the same first strand mixture as an internal equal loading control with oligo Tubulin forward (CTT GCA TTG GTA CAC AGG (SEQ ID NO. 10)) and Tubulin reverse (ACT TGA AAC CCA CGC TCC TC (SEQ ID NO. 11)) (GenBank accesion # U91564). To exclude that DNA may be amplified from contaminant DNA in the RNA sample, PCR control is set up with total RNA samples without reverse transcription.

Northern blot analyses (Sambrook et al. 1989) is used for detection of pr gene expression. Tobacco pr-1 and pr-2 gene probes were kindly provided by Dr. Yinong Yang (Department of Plant Pathology, University of Arkansas) and Dr. Santanu Dasgupta (Department of Agronomy, University of Kentucky), respectively, and are [$\alpha$-$^{32}$P]-dCTP labeled using a random labeling kit (Stratagene). 20 μg of total RNA from each treatment are fractionated in a 1.0% agarose/formaldehyde gel and subsequently blotted to Nytran Plus membranes. Hybridizations are performed with the appropriate probes in Northern MAX Prehyb/Hyb Buffer (Ambion Inc.) according to the manufacturer's instruction.

Salicylic Acid Detection

Salicylic acid (SA) assays are basically done as described (Bowling et al., 1994 and Gaffney et al., 1993). Briefly, 0.5 g leaf is ground in liquid $N_2$, then methanol extracted. The extract is dried and the pellet resuspended in 5% TCA. After spin, the supernatant is partitioned with organic mixture (ethyl acetate:cyclopentane:isopropanol, 50:50:1). The organic phase is dried, and the pellet resuspended in mobile phase (20 mM sodium acetate, pH 5.0, 20% methanol, 250 l) for HPLC analysis. For total SA, the TCA resuspended sample is heated in boiling water bath for 30 minutes then extracted with the organic mixture. 20 μl of SA sample is injected to a C18 HPLC column and quantified with Waters (Milford, Miss.) fluorescence detector with the Millennium program.

Pathogen Resistance Assays

Tobacco vein mottling virus (TVMV) and tobacco etch virus (TEV) inocula are prepared by grinding virus-infected tobacco leaves in water (1 g infected leaf tissue per 100 ml distilled water). The surface of the fifth leaf (from top of the plant) is dusted with carborundum and then rubbed with a gauze pad moistened with a virus suspension. Five plants are used for each treatment. Two weeks later, the disease symptoms are scored at the top new leaves. To further analyze the presence of virus on the top leaves, two leaf discs (about 100 mg) are taken from top leaf and ground in 100 μl SDS-polyacrylamide gel electrophoresis (PAGE) loading buffer. 20 μl of the supernatant is loaded to each gel well. Western blot analysis of the viral coat proteins is described in detail elsewhere (Fellers et al., 1998).

*Pseudomonas syringae* pv. *tabaci* WF4 is grown in liquid Luria Bertani (LB) medium at 28° C. overnight, collected by centrifugation, and resuspended in 10 mM MgCl2, and adjusted to cell density of OD600=1.0. For bacterial growth assay, the bacterial suspension is diluted 5,000 times and used to infiltrate the number 5 leaf from the top. Samples of inoculated tissue are taken daily by excision with a 6 mm cork borer. Bacteria inside the leaf discs are released by grinding the tissue in a microfuge tube in sterile water and plated on LB medium. Bacterial population is determined based on the number of colonies formed in LB plates, as described by Bertoni and Mills (1987). The mean values from three plates for each of three independent inoculations are presented. For disease symptom observation, the OD600=1.0 bacterial suspension is diluted 1,000, 5,000 and 10,000 times, then 10 μl are infiltrated to the leaves. Disease symptoms are photographed at the time indicated.

*Phytophthora parasitica* var. *nicotianae* isolate 62 (kindly provided by Ms. B. Kennedy, University of Kentucky) is grown on an oatmeal medium (5% Gerber oatmeal and 2% agar, w/v) plate. After the fungal mycelia has spread throughout the plate (~7 days), a plug of medium containing the fungal mycelia is made by excision with a 6 mm cork borer. A piece of tobacco leaf (the $5^{th}$ leaf from top) is cut into the size of a 9 cm petri dish, and placed upside down on top of a piece of water-soaked Whatman paper. The mycelium-agar plugs are set on the leaf disc with the mycelium side contacting with the leaf surface. The dish is sealed and set at 28° C. with 16 hr lightness and 8 hr darkness. Leaves are photographed four days after inoculation.

Although the present invention has been fully described by way of examples with reference to the accompanying drawings, it is to be noted that various changes and modifications will be apparent to those skilled in the art. It is therefore intended that it is the following claims, including all equivalents, which are intended to define the scope of this invention. Therefore, unless such changes and modifications depart from the scope of the present invention, they should be construed as being included therein.

REFERENCES

Alfano, J. R., Kim, H-S., Delanney, T. P. and Collmer, A., Evidence that the *Pseudomonas syringae* pv. *syringae* hrp-linked hrmA gene encodes an Avr-like protein that acts in an hrp-dependent manner within tobacco cells, *Mol. Plant Microbe Interact.*, 10: 580–588 (1997).

Bertoni, G., and Mills, D., A simple method to monitor growth of bacterial populations in leaf tissue, *Phytopathology*, 77: 832–835 (1987).

Bonas, U. and Van den Ackerveken, G., Gene for gene interaction: bacterial avirulence proteins specifiy plant disease resistance, *Curr. Opin. Microbiol*, 2: 94–98 (1999).

Bowling, S. A., Clarke, J. D., Liu, Y., Klessig, D. F., and Dong, X., The cpr5 mutant of Arabidopsis expresses both NPR1 -dependent and NPR1-independent resistance, *Plant Cell*, 9: 1573–1584 (1997).

Bowling, S. A., Guo, A., Gordon, A. S., Klessig, D. F., and Dong, X., A mutation in Arabidopsis that leads to constitutive expression of systemic acquired resistance, *Plant Cell*, 6: 1845–1857 (1994).

Clarke, J. D., Liu, Y., Klessig, D. F. and Dong, X., Uncoupling PR gene expression from NPR1 and bacterial resistance: Characterization of the dominant Arabidopsis cpr6-1 mutan, *Plant Cell*, 10: 557–569 (1997).

Collmer, A., Determinants of pathogenicity and avirulence in plant pathogenic bacteria, *Curr. Opin. Plant Biol.*, 1: 329–335 (1998).

Cornelissen, B. J. C., Hooft van Huijsduijinen, R. A. M., Van Loon, L. C., and Bol, J. F., Molecular characterization of messenger RNAs for 'pathogenesis-related' proteins 1a, 1b and 1c, induced by TMV infection of tobacco, *EMBO J.*, 5: 37–40 (1986).

Dangl, J. L., Dietrich, R. A., Richberg, M. H., Death don't have no mercy: cell death programs in plant-microbe interactions, *Plant Cell,* 8: 1793–1807 (1996).

Dietrich, R. A., Delaney, T. P., Uknes, S. J., Ward, E. R., Ryals, J. A., and Dangl, J. L., Arabidopsis mutants simulating disease resistance response, *Cell,* 77: 565–577 (1994).

Fellers, J., Collins, G. B. and Hunt, A. G., The Nia-proteinase of different potyviruses provide specific resistance to virus infection, *Crop Sci.,* 38: 1309–1319 (1998).

Gaffney, T., Friedrich, L., Vernooij, B., Negrotto, D., Nye, G., Uknes, S., Ward, E., Kessmann, H. and Ryals. J., Requirement of salicylic acid for the induction of systemic acquired resistance, *Science,* 261: 754–756 (1993).

Goodman, R. N., and Novacky, A. J., The hypersensitive reaction in plants to pathogens: a resistance phenomenon, *APS Press,* St. Paul, Minn. (1994).

Gopalan, S., Bauer, D. W., Alfano, J. R., Loniello, A. O., He, S. Y. and Collmer, A., Expression of the *Pseudomonas syringae* avirulence protein AvrB in plant cells alleviates its dependence on the hypersensitive response and pathogenicity (Hrp) secretion system in eliciting genotype-specific hypersensitive cell death, *Plant Cell,* 8: 1095–1105 (1996).

Greenberg, J. T., Guo, A., Klessig, D. F., and Ausubel, F. M., Programmed cell death in plants: A pathogen-triggered response activated coordinately with multiple defense fuctions, *Cell,* 77: 551–563 (1994).

He, S. Y., Type III protein secretion systems in plant and animal pathogenic bacteria, *Annu. Rev. Phytopathol,.* 36: 363–392 (1998).

Heu, S. and Hutcheson, S. W., Nucleotide sequence and properties of the hrm A locus associated with the *Pseudomonas syringae* pv. *syringae* 61 hrp gene cluster, *Mol. Plant Microbe Interact,* 6: 553–564 (1993).

Hoisington, D. A., Neuffer, M. G., and Walbot, V., Disease lesion mimic in maize, *Dev. Biol.,* 93: 381–388 (1982).

Lamb, C. and Dixon, R. A., The oxidative burst in plant disease resistance, *Annu. Rev. Plant Physiol. Plant Mol. Biol.,* 48: 251–275 (1997).

Leach J. E. and White F. F., Bacterial avirulence genes, *Annu. Rev. Phytopathol.,* 34: 153–179 (1996).

Li, Q. and Hunt, A. G., A near upstream element in a plant polyadenylation signal consists of more than six bases, *Plant Mol. Biol.,* 28: 927–934 (1995).

Maiti, I. B., Murphy, J. F., Shaw, J. G., and Hunt, A. G., Plants that express a potyvirus proteinase gene are resistant to virus infection, *Proc. Natl. Acad. Sci.,* USA, 90: 6110–6114 (1993).

Neuffer, M. G., and Calvert, O. H., Dominant disease lesion mimics in maize, *J. Hered.,* 66: 265–270 (1975).

Opperman, C. H., C. G. Taylor, and Conkling, M. A., Root-knot nematode-directed expression of a plant root-specific gene, *Science,* 263: 221–223 (1994).

Sambrook, J., Fritsch, E. F., and Maniatis, T., Molecular Cloning, A laboratory manual, Second edition, Cold Spring Harbor Laboratory Press (1989).

Staskawicz, B. J., Asubel, F. M., Bakerm, B. J., Ellis, J. E. & Jones, J. D. G., Molecular genetics of plant disease resistance, *Science,* 268: 661–667 (1995).

Sticher, L., B. Mauch-Mani, J. P. Metrauz. (1997). Systemic acquired resistance. Ann. Rev. Phytopathol 35, 235–270.

Walbot, V., Hoisington, D. A., and Neuffer, M. G., Disease lesion mimics in maize, *InGenetic Engineering of Plants,* T. Kosuge and C. Meredith, eds (New York: Plenum Publishing Company), pp. 431–442 (1983).

Wolter, M., Hollricher, K., Salamini, F., and Schulze-Lefert, P., The mlo resistance alleles to powdery mildew infection in barley trigger a developmentally controlled defence mimic phenotype, *Mol. Gen. Genet. ,* 239: 122–128 (1993).

Xu, D., Collins, G. B., Hunt, A. G., and Nielsen, M. T., Resistance to alfalfa mosaic virus in transgenic burley tobacco expressing the AMV coat protein gene, *Crop Sci.,* 38: 1661–1668 (1998).

---

What is claimed is:

1. An expression system comprising a Δ0.3TobRB7 promoter in operable linkage with a HrmA nucleotide having a sequence comprising the sequence set forth in SEQ ID NO.1.

2. A plant cell transformed with the expression system according to claim 1.

3. A transgenic plant transformed with the expression system according to claim 1.

4. A method for eliciting a hypersensitive response in plant cells, comprising:

(a) growing plant cells transformed with the expression system according to claim 1; and (b) expressing HrmA protein in said plant cells, wherein the expression of HrmA protein from said expression system results in a hypersensitive response in said plant cells.

5. A method for eliciting a hypersensitive response in a transgenic plant, comprising:

(a) obtaining a transgenic plant, wherein cells of the transgenic plant have been transformed with the expression system according to claim 1; and (b) expressing HrmA protein in said plant, wherein the expression of HrmA protein from said expression system results in a hypersensitive response in said plant.

6. A host cell, comprising the expression system according to claim 1.

7. A method of increasing resistance of a plant or plant cells to a pathogen selected from the group consisting of bacterial, fungal and viral pathogens, comprising:

(a) growing a plant or plant cells transformed with the expression system according to claim 1; and (b) expressing HrmA protein in said plant or plant cells,
   (i) wherein the expression of HrmA protein from said expression system results in increased resistance of a plant or plant cells to a pathogen by said plant, as compared to a plant or plant cells not containing said construct; and
   (ii) wherein said pathogen is selected from the group consisting of bacterial, fungal and viral pathogens.

* * * * *

SEQUENCE LISTING

<160> NUMBER OF SEQ ID NOS: 11

<210> SEQ ID NO 1
<211> LENGTH: 1128
<212> TYPE: DNA
<213> ORGANISM: Pseudomonas syringae

<400> SEQUENCE: 1

```
gtgaaccta  tccatgcacg  cttctccagc  gtagaagcgc  tcagacattc  aaacgttgat    60
attcaggcaa  tcaaatccga  gggtcagttg  gaagtcaacg  gcaagcgtta  cgagattcgt   120
gcggccgctg  acggctcaat  cgcggtcctc  agacccgatc  aacagtccaa  agcagacaag   180
ttcttcaaag  gcgcagcgca  tcttattggc  ggacaaagcc  agcgtgccca  aatagcccag   240
gtactcaacg  agaaagcggc  ggcagttcca  cgcctggaca  gaatgttggg  cagacgcttc   300
gatctggaga  agggcggaag  tagcgctgtg  ggcgccgcaa  tcaaggctgc  cgacagccga   360
ctgacatcaa  aacagacatt  tgccagcttc  cagcaatggg  ctgaaaaagc  tgaggcgctc   420
gggcgatacc  gaaatcggta  tctacatgat  ctacaagagg  gacacgccag  acacaacgcc   480
tatgaatgcg  gcagagtcaa  gaacattacc  tggaaacgct  acaggctctc  gataacaaga   540
aaaaccttat  catacgcccc  gcagatccat  gatgatcggg  aagaggaaga  gcttgatctg   600
```

-continued

```
ggccgataca tcgctgaaga cagaaatgcc agaaccggct tttttagaat ggttcctaaa    660
gaccaacgcg cacctgagac aaactcggga cgacttacca ttggtgtaga acctaaatat    720
ggagcgcagt tggccctcgc aatggcaacc ctgatggaca agcacaaatc tgtgacacaa    780
ggtaaagtcg tcggtccggc aaaatatggc cagcaaactg actctgccat tctttacata    840
aatggtgatc ttgcaaaagc agtaaaactg ggcgaaaagc tgaaaaagct gagcggtatc    900
cctcctgaag gattcgtcga acatacaccg ctaagcatgc agtcgacggg tctcggtctt    960
tcttatgccg agtcggttga agggcagcct ccagccacg gacaggcgag aacacacgtt    1020
atcatggatg ccttgaaagg ccagggcccc atggagaaca gactcaaaat ggcgctggca    1080
gaaagaggct atgacccgga aaatccggcg ctcagggcgc gaaactga              1128
```

<210> SEQ ID NO 2
<211> LENGTH: 375
<212> TYPE: PRT
<213> ORGANISM: Pseudomonas syringae

<400> SEQUENCE: 2

```
Met Asn Pro Ile His Ala Arg Phe Ser Ser Val Glu Ala Leu Arg His
 1               5                  10                  15

Ser Asn Val Asp Ile Gln Ala Ile Lys Ser Glu Gly Gln Leu Glu Val
             20                  25                  30

Asn Gly Lys Arg Tyr Glu Ile Arg Ala Ala Ala Asp Gly Ser Ile Ala
         35                  40                  45

Val Leu Arg Pro Asp Gln Gln Ser Lys Ala Asp Lys Phe Phe Lys Gly
     50                  55                  60

Ala Ala His Leu Ile Gly Gly Gln Ser Gln Arg Ala Gln Ile Ala Gln
 65                  70                  75                  80

Val Leu Asn Glu Lys Ala Ala Ala Val Pro Arg Leu Asp Arg Met Leu
                 85                  90                  95

Gly Arg Arg Phe Asp Leu Glu Lys Gly Gly Ser Ser Ala Val Gly Ala
            100                 105                 110

Ala Ile Lys Ala Ala Asp Ser Arg Leu Thr Ser Lys Gln Thr Phe Ala
        115                 120                 125

Ser Phe Gln Gln Trp Ala Glu Lys Ala Glu Ala Leu Gly Arg Tyr Arg
    130                 135                 140

Asn Arg Tyr Leu His Asp Leu Gln Glu Gly His Ala Arg His Asn Ala
145                 150                 155                 160

Tyr Glu Cys Gly Arg Val Lys Asn Ile Thr Trp Lys Arg Tyr Arg Leu
                165                 170                 175

Ser Ile Thr Arg Lys Thr Leu Ser Tyr Ala Pro Gln Ile His Asp Asp
            180                 185                 190

Arg Glu Glu Glu Glu Leu Asp Leu Gly Arg Tyr Ile Ala Glu Asp Arg
        195                 200                 205

Asn Ala Arg Thr Gly Phe Phe Arg Met Val Pro Lys Asp Gln Arg Ala
    210                 215                 220

Pro Glu Thr Asn Ser Gly Arg Leu Thr Ile Gly Val Glu Pro Lys Tyr
225                 230                 235                 240

Gly Ala Gln Leu Ala Leu Ala Met Ala Thr Leu Met Asp Lys His Lys
                245                 250                 255

Ser Val Thr Gln Gly Lys Val Val Gly Pro Ala Lys Tyr Gly Gln Gln
            260                 265                 270

Thr Asp Ser Ala Ile Leu Tyr Ile Asn Gly Asp Leu Ala Lys Ala Val
        275                 280                 285
```

```
Lys Leu Gly Glu Lys Leu Lys Lys Leu Ser Gly Ile Pro Pro Glu Gly
    290                 295                 300

Phe Val Glu His Thr Pro Leu Ser Met Gln Ser Thr Gly Leu Gly Leu
305                 310                 315                 320

Ser Tyr Ala Glu Ser Val Glu Gly Gln Pro Ser Ser His Gly Gln Ala
                325                 330                 335

Arg Thr His Val Ile Met Asp Ala Leu Lys Gly Gln Gly Pro Met Glu
                340                 345                 350

Asn Arg Leu Lys Met Ala Leu Ala Glu Arg Gly Tyr Asp Pro Glu Asn
        355                 360                 365

Pro Ala Leu Arg Ala Arg Asn
    370                 375

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Includes
      Promoter

<400> SEQUENCE: 3
cacgaagctt accatggacc ctatccatgc                                    30

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Includes
      promoter

<400> SEQUENCE: 4
tccgccgcgg ggtgaaccct atccatgc                                      28

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Includes
      promoter

<400> SEQUENCE: 5
gtggagctca gtttcgcgcc ctgag                                         25

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Includes
      promoter

<400> SEQUENCE: 6
ggaattcagc ttatctaaac aaagttttaa attc                               34

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Includes
      promoter
```

-continued

```
<400> SEQUENCE: 7
gtaagcttct gagcgatcct tctcactaga aaaatgc                              37

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Includes
      promoter

<400> SEQUENCE: 8
cacgaagctt accatgggat tttttctctt ttcac                                35

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Includes
      promoter

<400> SEQUENCE: 9
tcccgcggga gttttgggca tgagaag                                         27

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primers

<400> SEQUENCE: 10
cttgcattgg tacacagg                                                   18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primers

<400> SEQUENCE: 11
acttgaaacc cacgctcctc                                                 20
```